US00PP31571P2

(12) United States Plant Patent
Smit

(10) Patent No.: US PP31,571 P2
(45) Date of Patent: Mar. 17, 2020

(54) ***CRASSULA* 'EC-CRAS-1802'**

(50) Latin Name: *Crassula pubescens*
Varietal Denomination: EC-CRAS-1802

(71) Applicant: Obed Smit, Sappemeer (NL)

(72) Inventor: Obed Smit, Sappemeer (NL)

(73) Assignee: Eden Collection BV (NL)

( * ) Notice: Subject to any disclaimer, the term of this patent is extended or adjusted under 35 U.S.C. 154(b) by 0 days.

(21) Appl. No.: 16/350,694

(22) Filed: Dec. 18, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Crassula* cultivar named 'EC-CRAS-1802' is disclosed, characterized by distinct dense pubescence giving an overall grey sheen to the foliage. Leaf formation occurs in a unique pattern, alternating concentrically. The new variety is a *Crassula*, part of the Crassulaceae complex that includes *Crassula,l Pachyphytum, Graptopetalum, Sedum* and others. *Crassula* is a popular genus, typically produced as container plants or as landscape plants.

2 Drawing Sheets

Figure 1:
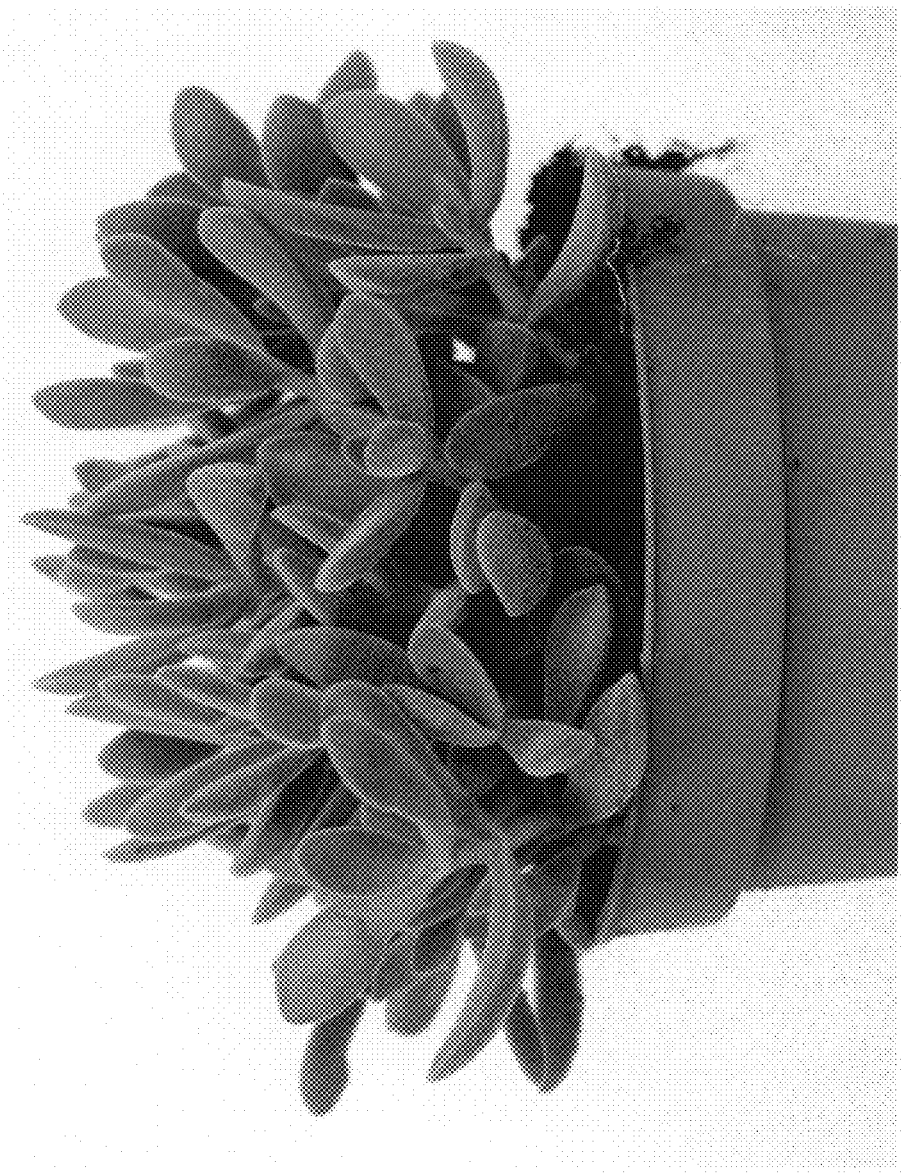

Latin name of the genus and species: *Crassula pubescens*.
Variety denomination: 'EC-CRAS-1802'.

BACKGROUND OF THE INVENTION

The new cultivar, *Crassula* 'EC-CRAS-1802', is the result of a planned breeding program by the inventor in a nursery in Sappemeer, the Netherlands. The objective was to produce distinct and better performing varieties of *Crassula pubescens*. The crossing resulting in the new cultivar is the result of crossing two unnamed, unpatented *Crassula pubescencs* varieties during 2014. The new variety was selected by the inventor, Obed Jacob Smit, in 2015.

Asexual reproduction of the new cultivar 'EC-CRAS-1802' was first performed in Sappemeer, the Netherlands, at a commercial greenhouse, by vegetative terminal cuttings in October of 2015. 'EC-CRAS-1802' has since produced multiple generations and has shown that the unique features of this cultivar are stable and reproduced true to type.

SUMMARY OF THE INVENTION

The cultivar 'EC-CRAS-1802' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-CRAS-1802' These characteristics in combination distinguish 'EC-CRAS-1802' as a new and distinct *Crassula* cultivar:

1. Distinct dense, grey pubescence gives the leaves and plant a distinct appearance.
2. Unique pattern of leaf-formation, alternating concentrically.

PARENTAL COMPARISON

Plants of the new cultivar 'EC-CRAS-1802' are similar to plants of the seed parent, *Crassula pubescens*, referred to as 'Plant A', unpatented, in most horticultural characteristics, however, plants of the new cultivar 'EC-CRAS-1802' differ in the following:

1. New cultivar has distinctly grey hairs; parent has grey-green hairs.
2. New cultivar has a concentrically alternating leaf formation; seed parent does not, producing leaves in a random pattern.

Plants of the new cultivar 'EC-CRAS-1802' are similar to plants of the pollen parent, *Crassula pubescens*, referred to as 'Plant B', unpatented, in most horticultural characteristics, however, plants of the new cultivar 'EC-CRAS-1802' differ in the following:

1. New cultivar has a concentrically alternating leaf formation; pollen parent does not.

COMMERCIAL COMPARISON

Plants of the new cultivar 'EC-CRAS-1802' are comparable to *Crassula pubescens* spp. radicans. The two *Crassula* are similar in most horticultural characteristics; however, the new variety 'EC-CRAS-1802' differs in the following:

1. New variety has green leaves with grey hairs; comparator has green and red leaves.
2. New variety has a hairy leaf surface; comparator has a smooth leaf surface.

Plants of the new cultivar 'EC-CRAS-1802' are comparable to *Crassula pubescens* spp. *rattrayi*. The two *Crassula* are similar in most horticultural characteristics; however, the new variety 'EC-CRAS-1802' differs in the following:

1. New cultivar's hairs are greyer than this comparator's.
2 New variety's hairs are smaller and shorter than the hairs of this comparator.

Plants of the new cultivar 'EC-CRAS-1802' are comparable to *Crassula arborescens* 'AMICRA1701', U.S. Pat. No. 30,749. The two *Crassula* varieties are similar in most horticultural characteristics; however, the new variety 'EC-CRAS-1802' differs in the following:

1. New variety has green leaves with grey hairs; comparator has green-red leaves.
2. New variety has a hairy leaf surface; comparator has a smooth leaf surface.
3. Plants of the new variety grow more densely.

BRIEF DESCRIPTION OF THE PHOTOGRAPHS

The accompanying photograph in FIG. 1 illustrates in full color the new *Crassula* plant 'EC-CRAS-1802' as grown in a commercial greenhouse in Sappemeer, the Netherlands.

Figure 2:
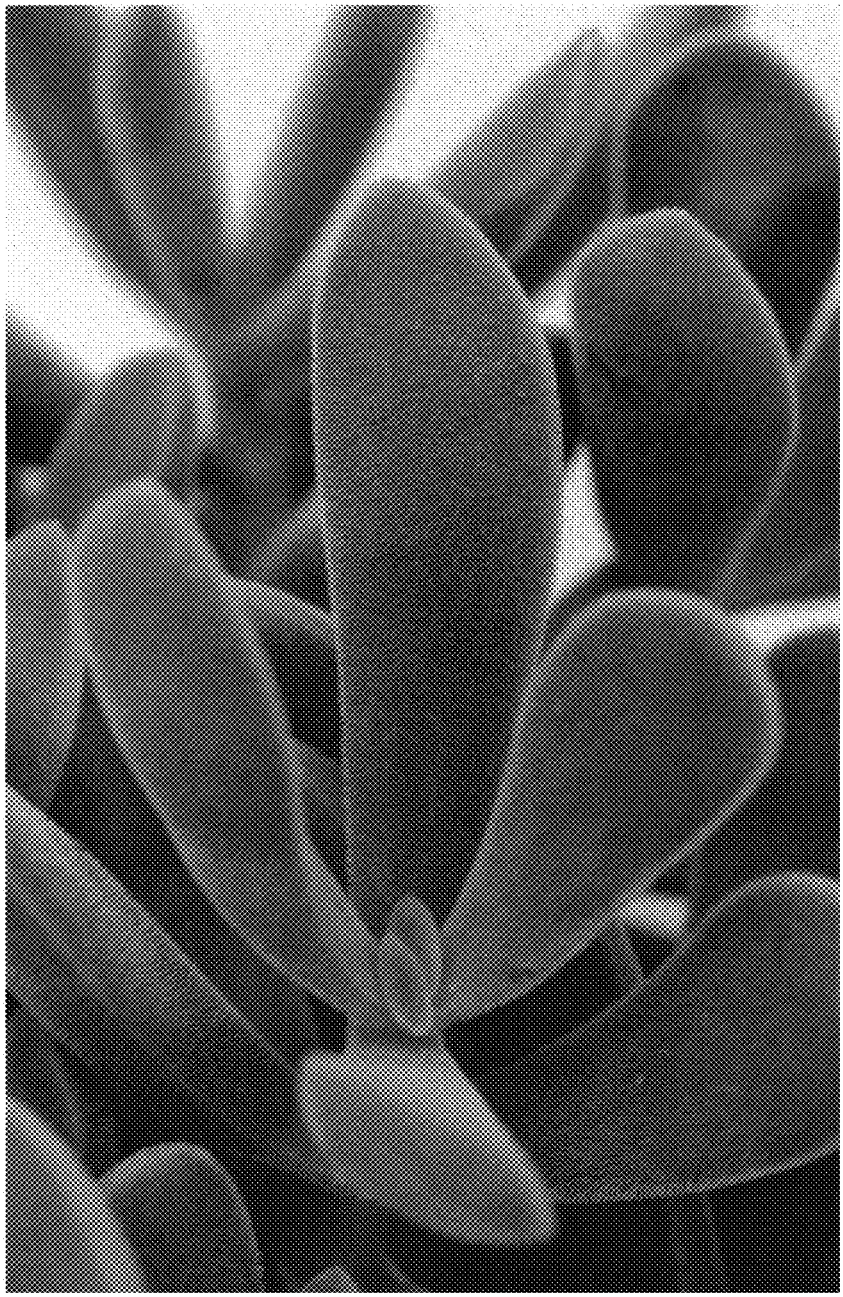

FIG. 2 illustrates a close-up of the variegation of the new *Crassula* plant 'EC-CRAS-1802' as grown in a commercial greenhouse in Sappemeer, the Netherlands. Age of the plant photographed is approximately 20 weeks from a well rooted cutting.

The photographs were taken using conventional techniques and although colors may appear different from actual colors due to light reflectance it is as accurate as possible by conventional photographic techniques. All photographs provided by breeder.

DETAILED BOTANICAL DESCRIPTION

In the following description, color references are made to Tthe Royal Horticultural Society Colour Chart 2015, except where general terms of ordinary dictionary significance are used. The following observations and measurements describe 'EC-CRAS-1802' plants in a commercial greenhouse in Sappemeer, the Netherlands. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Crassula pubescens* 'EC-CRAS-1802'.

PROPAGATION

Type of propagation typically used: Vegetative cuttings.

Time to initiate roots: About 7 to 10 days at approximately 21° C.,

Root description: Fibrous. White to tan, not accurately measured with the RHS chart.

PLANT

Age of plant described: 20 weeks.

Container size of the plant described: 10.5 cm.

Plant shape: Flattened, globular.

Growth habit: Broad spreading, upright.

Height: Average 8.7 cm.

Plant spread: Average 15.8 cm.

Growth rate: Low to moderate.

Branching characteristics: Main branches grow from the base, with lateral branches.

Number of primary branches: Average 10 per plant.

Number of secondary branches: Average 17 per plant.

Main branches:

*Length.*—Average: 5.0 cm.

*Diameter.*—Average: 0.3 cm.

*Internode length.*—Average: 1.2 cm.

Stems:

*Appearance and shape.*—Succulent, thick and rounded.

*Luster.*—Slightly glossy.

*Aspect/angle from vertical.*—Average angle to vertical: 25° (varying between 0° and 50°).

*Strength.*—Moderately weak.

*Color, developing.*—RHS Yellow-Green 145B.

*Color, mature.*—RHS Green 143C.

*Color at internodes.*—RHS Green 143C.

*Color of bark/older stems.*—Yellow-Green to Grey-Brown; a blend of RHS 152D and 199C, with 152D the dominate color.

*Pubescence.*—Stem densely covered with soft hairs, average length of hairs: 0.03 cm, colored green-white; too small to be measured with RHS accurately.

FOLIAGE

Leaf:

*Arrangement.*—Opposite.

*Compound or single.*—Single.

*Whole leaf length.*—Approximately 3.4 cm.

*Whole leaf width.*—Approximately 1.1 cm.

*Whole leaf shape.*—Oblanceolate, very slightly curved sideways and very slightly axillary twisted.

*Whole leaf aspect.*—Upper side very slightly convex, under side moderately concave, leaves succulent, average thickness: 0.6 cm.

*Apex.*—Broad acute.

*Base.*—Cuneate.

*Margin.*—Entire.

*Texture of top surface.*—Pubescent, succulent.

*Texture of bottom surface.*—Pubescent, succulent.

*Pubescence color.*—Overall appearance grey, near Black 202D. Individual hairs about 0.2 mm, too small to be accurately measured with the RHS chart.

*Quantity of leaves per lateral branch.*—Average 10 (5 pairs).

*Color.*—Leaf/leaflet color, young, upper side: RHS Green 143A, fading to RHS Yellow-Green 144B to 1440 towards the base. Leaf/leaflet color, young, under side: RHS Green 143B, fading to RHS Yellow-Green 144B towards the base. Leaf/leaflet color, mature, upper side: RHS Green 143A and darker. Leaf/leaflet color, mature, under side: RHS Green 143A, fading lighter towards the base to 143B.

*Venation.*—There is no visual appearance of venation.

FLOWER

Flowering not observed to date.

REPRODUCTIVE ORGANS

Flowering not observed to date.

OTHER CHARACTERISTICS

Fruits and seeds: Not observed to date.

Temperature tolerance: Tolerates temperatures from approximately −2° C. to 32° C.

Disease/pest resistance: No increased nor decreased resistance to normal diseases and pests of *Crassula* has been observed.

Drought tolerance: Tolerates at least 3 weeks of high temperatures without supplemental water, showing no serious damage to plant.

What is claimed is:

1. A new and distinct cultivar of *Crassula* plant named 'EC-CRAS-1802' as herein illustrated and described.

* * * * *